US00PP13774P29

(12) United States Plant Patent
Kolster

(10) Patent No.: US PP13,774 P2
(45) Date of Patent: May 6, 2003

(54) PHILADELPHUS PLANT NAMED 'SNOWWHITE FANTASY'

(75) Inventor: Peter R. Kolster, Boskoop (NL)

(73) Assignee: Gebr. Kolster BV, Boskoop (NL)

( * ) Notice: Subject to any disclaimer, the term of this patent is extended or adjusted under 35 U.S.C. 154(b) by 0 days.

(21) Appl. No.: 10/159,062

(22) Filed: May 31, 2002

(51) Int. Cl.[7] ..... A01H 5/00
(52) U.S. Cl. ..... Plt./226
(58) Field of Search ..... Plt./226

(56) References Cited

U.S. PATENT DOCUMENTS

PP2,703 P * 1/1967 Bergeron ..... Plt./226

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Philadelphus plant named 'Snowwhite Fantasy', characterized by its upright and outwardly spreading plant habit; freely branching growth habit; freely flowering habit; and numerous large showy double white flowers.

1 Drawing Sheet

BOTANICAL CLASSIFICATION/CULTIVAR DESIGNATION

*Philadelphus×virginalis* cultivar Snowwhite Fantasy.

BACKGROUND OF THE INVENTION

The present Invention relates to a new and distinct cultivar of Philadelphus plant, botanically known as *Philadelphus×virginalis,* and hereinafter referred to by the name 'Snowwhite Fantasy'.

The new Philadelphus was discovered as a cross-pollination of two unidentified selections of *Philadelphus× virginalis,* not patented. The new Philadelphus was discovered and selected by the Inventor in 1998 as a single flowering plant in a controlled environment in Boskoop, The Netherlands, within a population of the progeny resulting from the cross-pollination.

Asexual reproduction of the new Philadelphus by cuttings was first conducted in Boskoop, The Netherlands in 1998. Since then, asexual reproduction by cuttings has shown that the unique features of this new Philadelphus are stable and reproduced true to type in successive generations.

SUMMARY OF THE INVENTION

The cultivar Snowwhite Fantasy has not been observed under all possible environmental conditions. The phenotype may vary somewhat with variations in environment such as temperature and light intensity without, however, any variance in genotype.

The following traits have been repeatedly observed and are determined to be the unique characteristics of 'Snowwhite Fantasy'. These characteristics in combination distinguish 'Snowwhite Fantasy' as a new and distinct Philadelphus:

1. Upright and outwardly spreading plant habit.
2. Freely branching growth habit.
3. Freely flowering habit.
4. Numerous large showy double white flowers.

Plants of the new Philadelphus are more freely flowering than plants of the parent selections and other known selections and cultivars of *Philadelphus×virginalis.*

BRIEF DESCRIPTION OF THE PHOTOGRAPHS

The accompanying colored photographs illustrate the overall appearance of the new Philadelphus showing the colors as true as it is reasonably possible to obtain in colored reproductions of this type. Colors in the photographs may differ from the color values cited in the detailed botanical description which accurately describe the colors of the new Philadelphus.

The photograph at the top of the sheet comprises a side perspective view of a typical flowering plant of 'Snowwhite Fantasy' grown in an outdoor nursery.

The photograph at the bottom of the sheet is a close-up view of a typical flower of 'Snowwhite Fantasy'.

DETAILED BOTANICAL DESCRIPTION

The aforementioned photographs and following observations and measurements describe plants grown in Boskoop, The Netherlands, in an outdoor nursery under full sun conditions. The photographs and the observations and measurements were taken during June, 2001; plants used for the photographs, observations and measurements were about three years old. During the summer, day temperatures averaged 18° C. and night temperatures averaged 10° C. Color references are made to The Royal Horticultural Society Colour Chart, 2001 edition, except where general terms of ordinary dictionary significance are used.

Botanical classification: *Philadelphus×virginalis* cultivar Snowwhite Fantasy.

Parentage:

*Female, or seed, parent.*—Unidentified selection of *Philadelphus×virginalis,* not patented.

*Male, or pollen, parent.*—Unidentified selection of *Philadelphus×virginalis,* not patented.

Propagation:

*Type.*—By cuttings.

*Time to initiate roots, summer.*—About 35 days at 17° C.

*Time to initiate roots, winter.*—About 80 days at 10° C.

*Time to produce a rooted plant, summer.*—*About* 100 days at 17° C.

*Time to produce a rooted plant, winter.*—About 140 days at 10° C.

*Root description.*—Dense, freely branching.

Plant description:

*Appearance.*—Perennial woody shrub. Upright and outwardly spreading plant habit; broad conical plant shape. Very freely branching; about 16 lateral branches develop per plant; dense and full plants. Moderately vigorous growth habit.

*Plant height.*—About 200 cm.

*Plant width or area of spread.*—About 150 cm.

*Lateral branches.*—Length: About 10 cm. Diameter: About 2 mm. Internode length: About 2.7 cm. Strength: Moderately strong. Texture: Smooth, glabrous. Color, immature: 144A to 144B. Color, mature: 199A to 199C.

*Foliage description.*—Arrangement: Opposite; single. Length: About 7.5 cm. Width: About 4.8 cm. Shape: Ovate to elliptic. Apex: Acute to apiculate. Base: Obtuse. Margin: Serrate. Venation pattern: Pinnate. Texture, upper and lower surfaces: Densely pubescent; slightly rugose. Color: Young and fully expanded foliage, upper surface: 137A. Young and fully expanded foliage, lower surface: 138A to 138B. Venation, upper surface: 137A. Venation, lower surface: 191B. Petiole: Length: About 8 mm. Diameter: About 1 mm. Texture, upper and lower surfaces: Glabrous. Color, upper and lower surfaces: 144A to 144B.

Flower description:

*Appearance.*—Solitary axillary double flowers. Flowers drooping. Flowers not persistent.

*Flowering response.*—Plants flower continuous and freely during the summer, typically mid-June in Boskoop, The Netherlands.

*Postproduction longevity.*—Individual flowers maintain good color and substance for about ten to 14 days on the plant when grown in an outdoor environment and for about 7 to 10 days as a cut flower in an interior environment.

*Quantity of flowers.*—Freely flowering; about 10 open flowers and flower buds per lateral stem per flowering season.

*Fragrance.*—Strong, pleasantly sweet.

*Flower bud.*—Length: About 1.8 cm. Diameter: About 1.2 cm. Shape: Ovoid. Color: 155C.

*Flower diameter.*—About 4.2 cm.

*Flower height* (*depth*).—About 2 cm.

*Petals.*—Quantity per flower: Four. Length: About 2.3 cm. Width: About 1.7 cm. Shape: Broadly obovate. Apex: Rounded. Base: Attenuate. Margin: Entire. Texture, upper and lower surfaces: Smooth, glabrous. Color: Developing and fully expanded petals, upper surface: 155C. Developing and fully expanded petals, lower surface: 155C.

*Petaloids.*—Quantity per flower: About 25. Length: About 2 cm. Width: About 9 mm. Shape: Elliptic to narrowly obovate or spatulate. Apex: Rounded. Base: Attenuate. Margin: Entire. Texture, upper and lower surfaces: Smooth, glabrous. Color: Developing and fully expanded petals, upper surface: 155C. Developing and fully expanded petals, lower surface: 155C.

*Sepals.*—Quantity per flower: Four. Length: About 9 mm. Width: About 4 mm. Shape: Triangular to deltoid. Apex: Aristate. Base: Broadly cuneate. Margin: Entire. Texture, upper and lower surfaces: Pubescent. Color: Developing and fully expanded sepals, upper surface: 138B. Developing and fully expanded sepals, lower surface: 138A.

*Peduncles.*—Length: About 8 mm. Diameter: About 1 mm. Orientation: About 40 to 50° from vertical. Strength: Strong. Color: 138A.

*Reproductive organs.*—Stamens: Quantity per flower: Occasionally one or two, typically deformed. Anther shape: Linear; basifixed. Anther length: About 1 mm. Anther color: Close to 9A. Pollen amount: Scarce. Pollen color: Close to 9A. Pistils: Quantity per flower: Four, fused towards the base. Pistil length: About 9 mm. Style length: About 9 mm. Style color: 155D. Stigma shape: Oblong, flattened. Stigma color: 155D. Ovary color: 154C.

*Fruits.*—Quantity per flower: One. Days to ripening: About 100. Type: Capsule. Length: About 1 cm. Diameter: About 6 mm. Texture: Smooth, glabrous. Color: 199A.

*Seeds.*—Length: About 4 mm. Diameter: About 2 mm. Texture: Smooth, glabrous. Color: N200A.

Disease resistance: Plants of the new Philadelphus have not been observed to be resistant to pathogens common to Philadelphus.

Temperature tolerance: Plants of the new Philadelphus have been observed to tolerate temperatures from about −23 to 38° C.

It is claimed:

1. A new and distinct cultivar of Philadelphus plant named 'Snowwhite Fantasy', as illustrated and described.

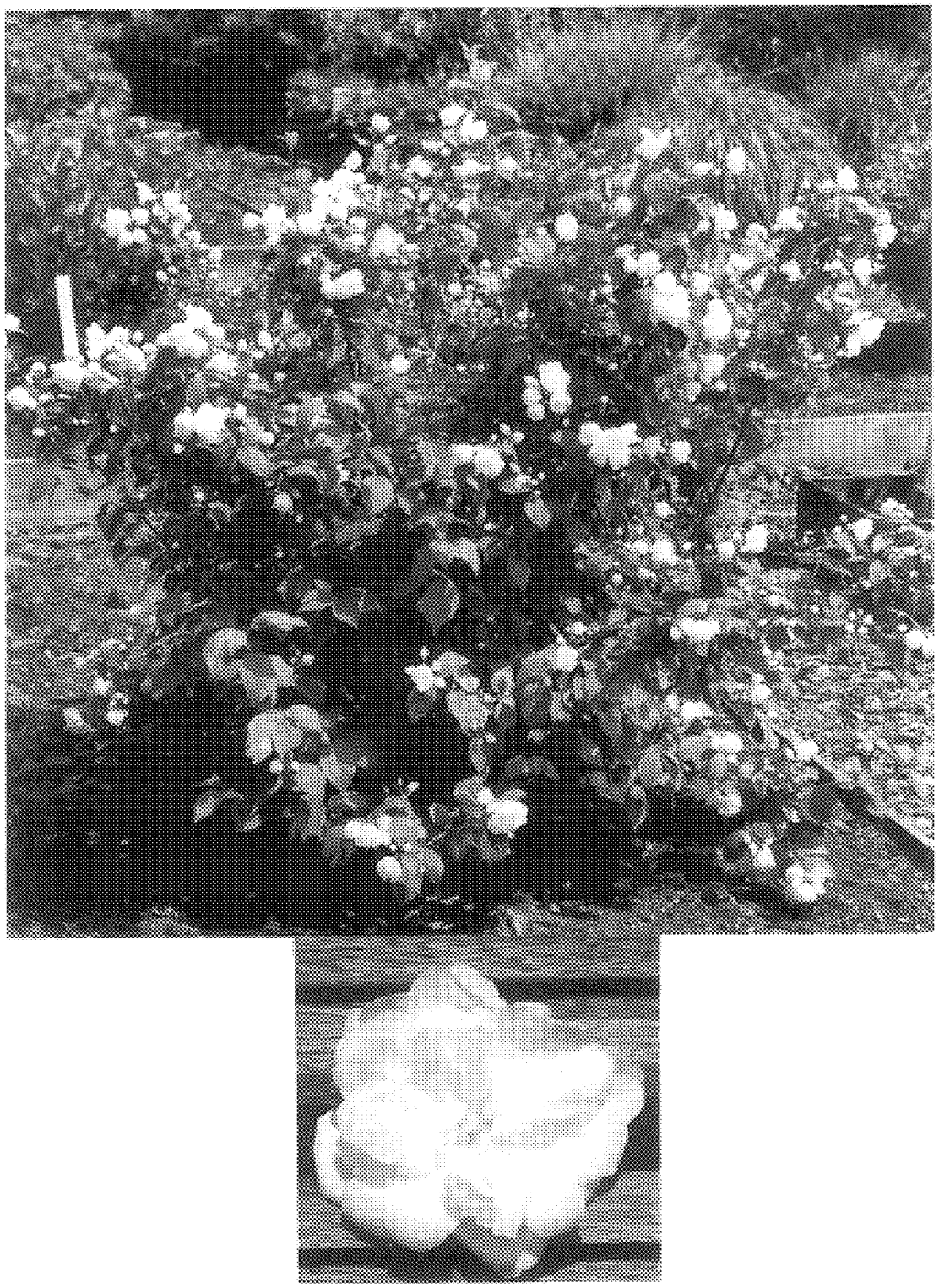

* * * * *